United States Patent
Diokno et al.

(10) Patent No.: US 6,470,890 B1
(45) Date of Patent: Oct. 29, 2002

(54) DEVICE AND A METHOD FOR MECHANICAL INSTALLATION AND REMOVAL OF INFLATABLE VAGINAL PESSARY

(76) Inventors: Ananias Diokno, 480 Hillspur Rd., Ann Arbor, MI (US) 48105; German Borodulin, 583 46th Ave., San Francisco, CA (US) 94121; Alexander Shkolnik, 485 Dartmouth Ave., San Carlos, CA (US) 94070

( * ) Notice: Subject to any disclaimer, the term of this patent is extended or adjusted under 35 U.S.C. 154(b) by 26 days.

(21) Appl. No.: 09/663,650

(22) Filed: Sep. 18, 2000

(51) Int. Cl.$^7$ .................................................. A61F 5/48
(52) U.S. Cl. ............................... 128/885; 128/DIG. 25; 600/29
(58) Field of Search ................................ 128/885, 886, 128/DIG. 25; 600/29–31

(56) References Cited

U.S. PATENT DOCUMENTS

| | | | | |
|---|---|---|---|---|
| 2,324,520 A | * | 7/1943 | Lamson | 128/DIG. 25 |
| 2,533,924 A | * | 12/1950 | Foley | 128/DIG. 25 |
| 3,642,004 A | * | 2/1972 | Osthagen | 128/DIG. 25 |
| 3,812,841 A | * | 5/1974 | Issacson | 128/DIG. 25 |
| 5,611,768 A | | 3/1997 | Tutrone | |
| 5,795,288 A | * | 8/1998 | Cohen | 600/29 |
| 6,119,697 A | * | 9/2000 | Engel | 128/885 |

OTHER PUBLICATIONS

Calog of Millex Products, Inc., Chicago, USA Pessaries of Various types.

* cited by examiner

*Primary Examiner*—Michael A. Brown

(57) ABSTRACT

An inflatable vaginal pessary of the invention, which can be mechanically inserted into and removed from the patient's vagina, comprises a tapered body inflatable at its large-diameter side and having an axial channel inflation of the pessary. This channel passes from the small-diameter end to the inflatable chamber and has a check valve at the outer end of the channel for inflation of the pessary. The pessary can be connected to and disconnected from a mechanism for insertion and removal of the pessary into and from the vaginal cavity. This mechanism has a hollow tubular housing with a funnel-like finder for engagement with the tapered end of the pessary. On the bottom of the finder the pessary installation mechanism has a threaded tubular stem that could be screwed into the threaded opening on the tapered end of the pessary. On the proximal end the mechanism has a pumping bulb for inflating the pessary via the check valve by squeezing the bulb, in the same manner as inflation of the occlusive cuff in a manually-operated blood-pressure measuring apparatus. The pessary of the invention can be easily installed into the patient's vagina by the patient herself. For this purpose, the pessary is connected to the aforementioned mechanism, inserted by the patient into an appropriate position inside her vagina, inflated to a required degree in order to fix the pessary in place, and is then disconnected from the mechanism for use during the day. In its inflated state with an increase diameter the pessary compresses the urethra through the vaginal wall and thus reduces the cross section of the urethral lumen. At the end of the day before the bed time, the patient easily reconnects the mechanism to the pessary, deflates the pessary, and removes the latter by means of the same mechanism.

20 Claims, 4 Drawing Sheets

DEVICE AND A METHOD FOR MECHANICAL INSTALLATION AND REMOVAL OF INFLATABLE VAGINAL PESSARY

TECHNICAL FIELD

The present invention relates to an inflatable vaginal pessary suitable for treating urinary incontinence, cystoceles, rectoceles, enteroceles, and uterine prolapse. The invention also relates to a method for installation and removing of the aforementioned inflatable pessary.

BACKGROUND

Continence, or normal control of urine retention in the bladder, involves the coordination of the bladder, bladder neck and urinary sphincter. The body stores urine in the bladder by maintaining a closed bladder neck and a contracted urinary sphincter muscle. To pass urine the bladder contracts while the bladder neck opens and the urinary sphincter muscle relaxes.

Urinary incontinence (UI) occurs when one or more of the anatomical structures related to urine storage malfunctions and leads to a loss of control of urination. The most common type of incontinence is caused by hypermobility of the bladder neck and urethra due to weakening of the tissues surrounding these structures. In females, pelvic trauma associated with child birth is a common cause of tissue weakening. Another cause of incontinence is a deficiency in urinary sphincter muscle control, intrinsic sphincter deficiency (ISD). It is estimated that approximately 8.5 million women suffer from UI in the United States. Up to 75% of female nursing home patients experience some degree of urinary incontinence, creating a tremendous economic, as well as hygienic, burden.

Female incontinence is currently treated using behavioral techniques, various devices, surgical techniques, and pharmaceuticals. Among devices widely used for alleviating the above problem, a device, which is known as pessary, is a useful alternative or an adjunctive aid rather than a substitute for gynecological surgery. A pessary is a device, which is inserted into the vagina for controlling uterine prolapse, uterine retrodisplacement, or stress urinary incontinence via the walls of the vagina.

A great variety of vaginal pessary device is known and is available on the market. Some pessaries are made in the form of a rigid, i.e., non-inflatable rings, dishes, hodges, donuts, etc. Such devices are produced, e.g., by Millex Products, Inc., Chicago, U.S.A. The aforementioned pessaries are inserted and removed manually which present a problem for inserting and removing by the patient. Insertion and removal of such pessary by the doctor or nurse is easy in most cases. In the past, doctors and nurses would fit the patient with a type of pessary, insert it into the patients vagina and leave it there for 3 months. The patient comes back to the doctor's office in 3 months and remove, clean and insert the pessary again or use a new one. But the doctor or nurse always insert and remove the pessary. Such a practice is seldom used now because pessaries left for weeks and months usually cause irritation and infection in the vagina and produce bad odor and significant vaginal discharge. Therefore most doctors and patient have abandoned this method.

The new approach is to use the pessary on a daily basis by having the patient insert the pessary in the morning and removing it in the evening. She cleans the pessary with special solution, and then re-insert it the next morning. This is the same idea as intermittent catheterization that is now done three-four times per day by the patient rather than having an indwelling Foley catheter in the bladder for usually four weeks, and the doctor insert and remove the catheter.

The problem with this new method of daily insertion and removal is that the patient has to learn how to insert and remove the pessary herself. However, as has been mentioned above, the aforementioned rigid pessaries are difficult to insert and likewise, very difficult to remove by the patient.

Attempts have been made to solve the above problem by providing an inflatable pessary consisting of a donut-type inflatable portion which is manually inserted into the vagina and which is connected via a flexible tube with an externally located pumping bulb. The donut portion is individually fitted and adjusted into a required place of the vagina and then is inflated to a proper size by means of the pumping bulb via the flexible tube. The donut portion is provided with a check valve for maintaining the pessary in an inflated state. Upon completion of inflation, the bulb is disconnected leaving a short piece of the flexible tube protruding out from the vagina, so that this protruding end can then be used for removing the inflated donut portion of the pessary from the vagina. Such a device is also produced by Millex Products, inc., Chicago, U.S.A. A disadvantage of this device is that it is still manually inserted and that the end of the flexible tube protruding from the vagina creates discomfort for the patient. Another disadvantage is that the donut portion is removed in an inflated state.

U.S. Pat. No. 5,611,768 issued in 1997 to R. Tutrone discloses a pessary device comprising two sequentially arranged inflatable chambers, one of which is placed into the anterior part of the vaginal cavity and another to the posterior part of the vaginal cavity. Both chambers are inflated separately via separate valves located outside the vagina and remaining attached to the device after the inflation. At least one of the chambers is intended for pressing via the vaginal wall on the urethra thus combating female incontinence.

This device entails the same disadvantages as the previously described pessaries, i.e., the pessary removing means remain permanently attached to the pessary. Another disadvantage is that this device has a complicated construction. It has top be manually inserted and removed.

OBJECTS OF THE INVENTION

It is an object of the invention to provide a mechanically insertable and removable inflatable vaginal pessary which is easily insertable and removable by a patient, which is disconnected from the insertion and removal device after inflation and during the use of the pessary, and which can be easily reconnected to the aforementioned device, and can be adjusted to a required position within the patient's vagina. It is another object to provide a mechanical device, which is connectable to a pessary for its insertion, disconnectable from the inserted pessary after insertion, and reconnectable for removal of the pessary for replacement. It is a further object to provide the aforementioned mechanical device with means for inflation and deflation of the inflatable pessary. Another object is to provide a method for easy and reliable insertion of the pessary by the patient herself.

SUMMARY OF THE INVENTION

An inflatable vaginal pessary of the invention, which can be mechanically inserted into and removed from the patient's vagina, comprises a tapered body inflatable at its large-diameter side and having an axial channel for inflation of the pessary. This channel passes from the small-diameter end to the inflatable chamber and has a check valve at the outer end of the channel for inflation of the pessary. The pessary can be connected to and disconnected from a mechanism for insertion and removal of the pessary into and from the vaginal cavity. This mechanism has a hollow tubular housing with a funnel-like finder for engagement with the tapered end of the pessary. On the bottom of the finder the pessary installation mechanism has a threaded tubular stem that could be screwed into the threaded opening on the tapered end of the pessary. On the proximal end the mechanism has a pumping bulb for inflating the pessary via the check valve by squeezing the bulb, in the same manner as inflation of the occlusive cuff in a manually-operated blood pressure measuring apparatus. The pessary of the invention can be easily installed into the patient's vagina by the patient herself. For this purpose, the pessary is connected to the aforementioned mechanism, inserted by the patient into an appropriate position inside her vagina, inflated to a required degree in order to fix the pessary in place, and is then disconnected from the mechanism for use during the day. In its inflated state with an increase diameter the pessary compresses the urethra through the vaginal wall and thus reduces the cross section of the urethral lumen. At the end of the day before the bedtime, the patient easily reconnects the mechanism to the pessary, deflates the pessary, and removes the latter by means of the same mechanism.

DETAILED DESCRIPTION OF THE INVENTION

A method of the invention comprises the steps of: providing an inflatable vaginal pessary, which has an inflatable portion with a check valve, a tapered guide portion with connection means, and a pessary insertion/removal device; connecting the aforementioned device to the aforementioned connection means of the pessary in a deflated state, when its inflatable portion has a reduced diameter; inserting the pessary into the patient's vagina; inflating the pessary within the vagina so as to fix it in place; disconnecting the pessary insertion/removal device from the pessary; maintaining the pessary within the vagina for a required period of time; connecting the aforementioned device to the aforementioned connection means of the pessary; deflating the inflatable portion by acting with the aforementioned device on the check valve of the pessary, thus reducing the diameter of the inflatable portion; removing the pessary from the vagina; and disconnecting the used pessary from the device for discarding.

Figure 1:
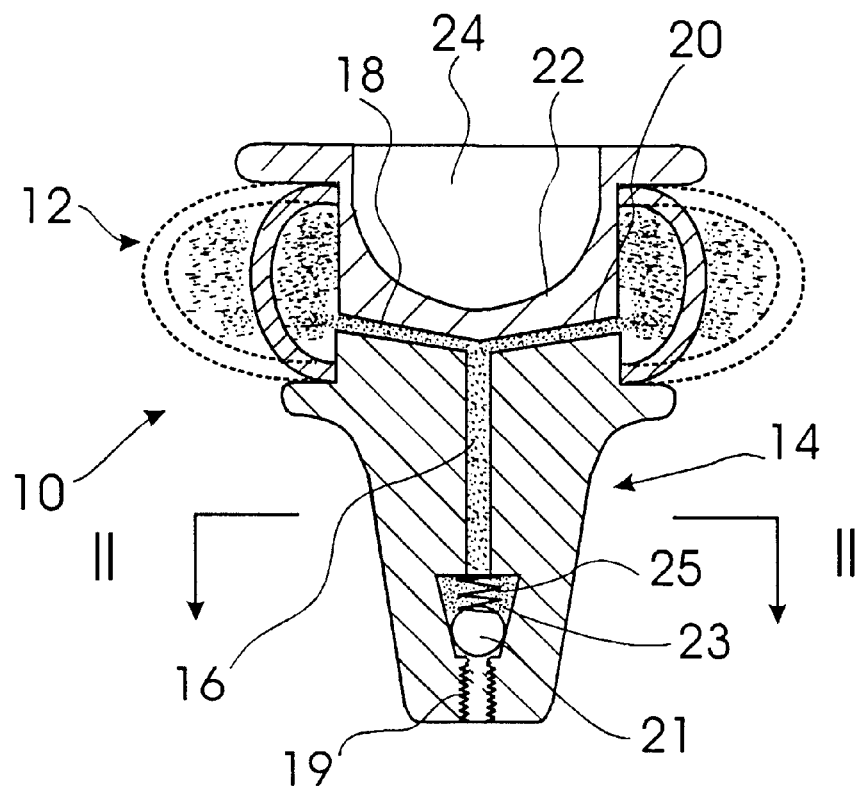
FIG. 1 is a longitudinal sectional view of an inflatable vaginal pessary in accordance with one embodiment of the invention.

An inflatable vaginal pessary for realization of the method of the invention is shown in FIG. 1, which is a longitudinal sectional view of the device. As can be seen from this drawing, the pessary consists of a donut-like hollow inflatable portion 12, shown by solid lines in an inflated form and by dash-and-dot lines in its inflated form, and a tapered guide portion 14 projecting from the inflatable portion 12. The tapered guide portion 14 has a longitudinal channel 16, which is open to the atmosphere at one end and is connected to the hollow inflatable portion 12 at the other end via transverse channels 18 and 20. It can also be seen that in the embodiment shown in FIG. 1 the tapered guide portion 14 of the vaginal pessary 10 has a round cross section.

Figure 2:
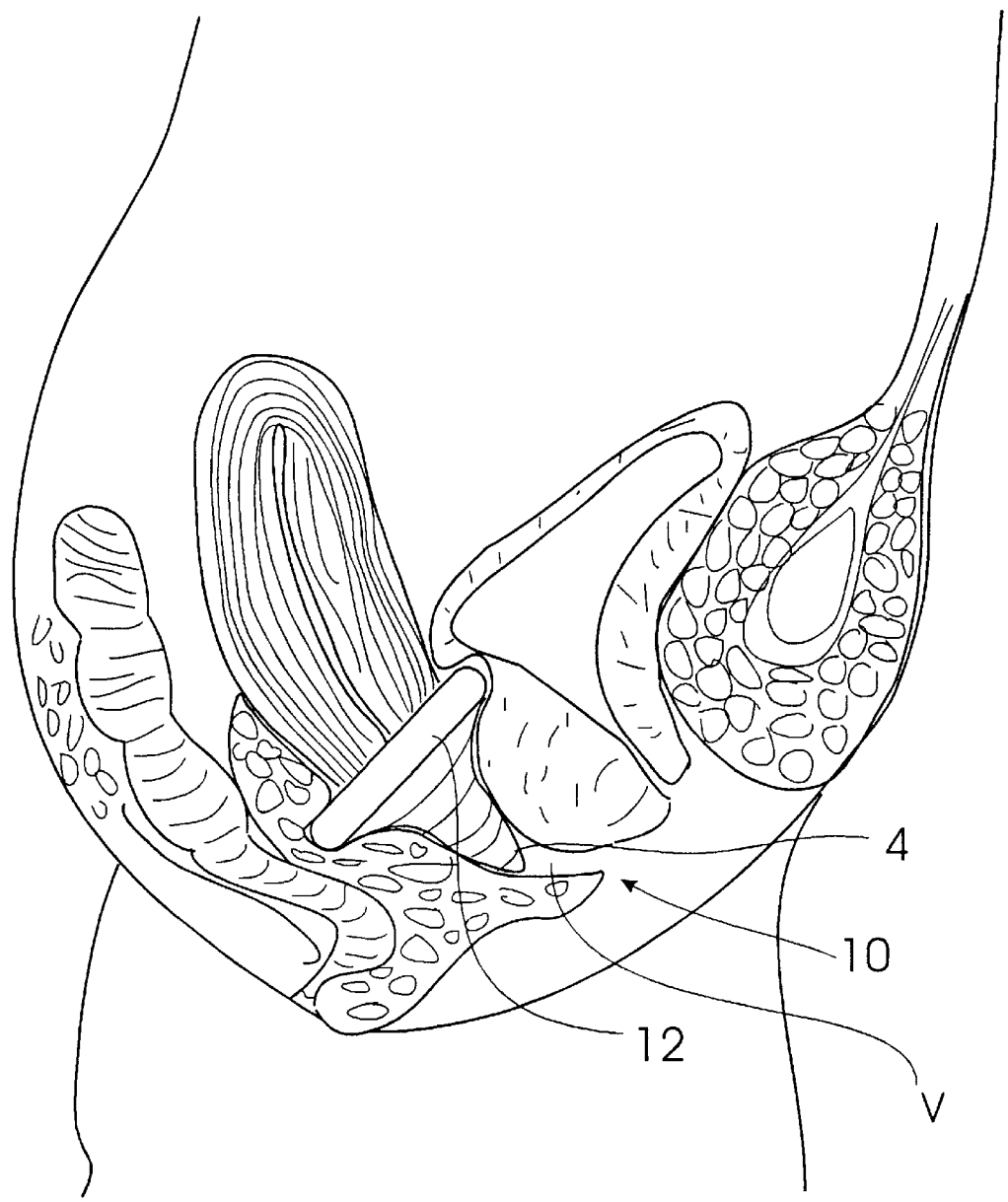
FIG. 2 is a view illustrating operating position of the inflatable pessary of FIG. 1 within the vaginal cavity of a patient.

At the end opposite to the inflatable portion 12 the longitudinal channel 16 has a threaded portion 19, and a spring-located ball 21 which is located in a tapered expansion 23 of the channel 16 is permanently urged by a spring 25 toward the threaded end of the channel 16 for normally closing the channel. The spring-loaded ball 21 forms a check valve which allows admission of the pressurized fluid into the channel for inflation of the inflated portion 12 but prevents the escape of pressurized fluid from the inflated pessary. On the side opposite to the tapered guide portion 14, the inflatable portion 12 is fit onto a bobbin-like end 22 of the tapered portion which has a recess 24 for engagement with neck of the uterus U when the pessary is installed and fixed in the vagina V in the operating position, as shown in FIG. 2.

Figure 3:
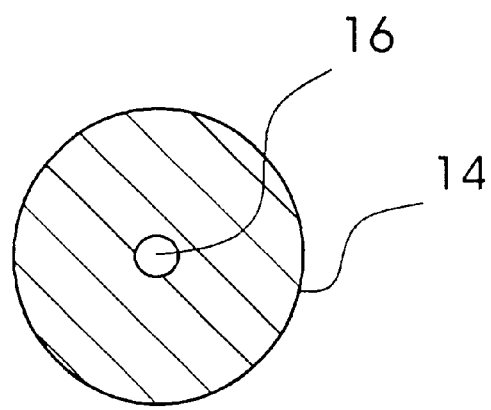
FIG. 3 is a sectional view along line III—III of FIG. 1.

FIG. 3 is a longitudinal sectional view of the inflatable pessary of FIG. 1 connected, prior to insertion into the patient's vagina, to a mechanical pessary insertion/removal device 30. The insertion/removal device 30 has a hollow tubular housing 32 with a longitudinal central opening 34 and a funnel-like pessary finder 36 on the end of the housing 32 that faces the pessary 10. On the finder side, the central opening 34 is closed with an end wall 38, which forms the bottom of the funnel-like finder 36. A threaded tubular stem 40, which has an external thread 42, extends from the outer side of the end wall 38 for engagement with the thread 19 at the end of the longitudinal channel 16 of the pessary 10. The length of the threaded tubular stem 40 is greater than the distance from the front end of the tapered portion 14 of the pessary to the spring-loaded ball 21 in it normal position. It is recommended that the threaded stem 40 and the threaded opening 19 have non-locking thread, which could be easily disconnected and reconnected without application of a noticeable torque.

At the end opposite to the finder 36, the tubular housing 32 of the insertion/removal device 30 has a flange 42 for use as a handle for connecting the device 30 to the pessary by screwing the threaded stem 40 into the threaded opening 19 of the pessary 10. On the flanged side, the housing 32 has a pumping bulb 44 made of a resilient material such as rubber for inflating the pessary 10 via the check valve of the pessary 10 formed by the spring-loaded ball 21 by squeezing the bulb 44, in the same manner as inflation of the occlusive cuff in a manually-operated blood-pressure measuring apparatus. The bulb 44 can be easily removed or connected by fitting onto spherical or similar head 46 with a through opening 47 connected to the central opening 34 of the housing 32. Reference numeral 45 designates a check valve in the bulb 44 for admission of air from the surrounding atmosphere when the bulb is released after being squeezed for pumping the inflatable portion of the pessary.

In order to ensure that the valve formed by the ball 21 is closed when the device 30 is connected to the pessary 10 prior to insertion into the patient's vagina, the pessary 10 may have a mark 48 on the outer surface of the tapered portion 14 for discontinuing rotation of the flange 42 when the front end of the finder 36 is aligned with the position of the mark 48. The same mark 48 can be used for deflation of the inflated portion 12 of the pessary prior to removal of the pessary from the vagina.

Figure 4:
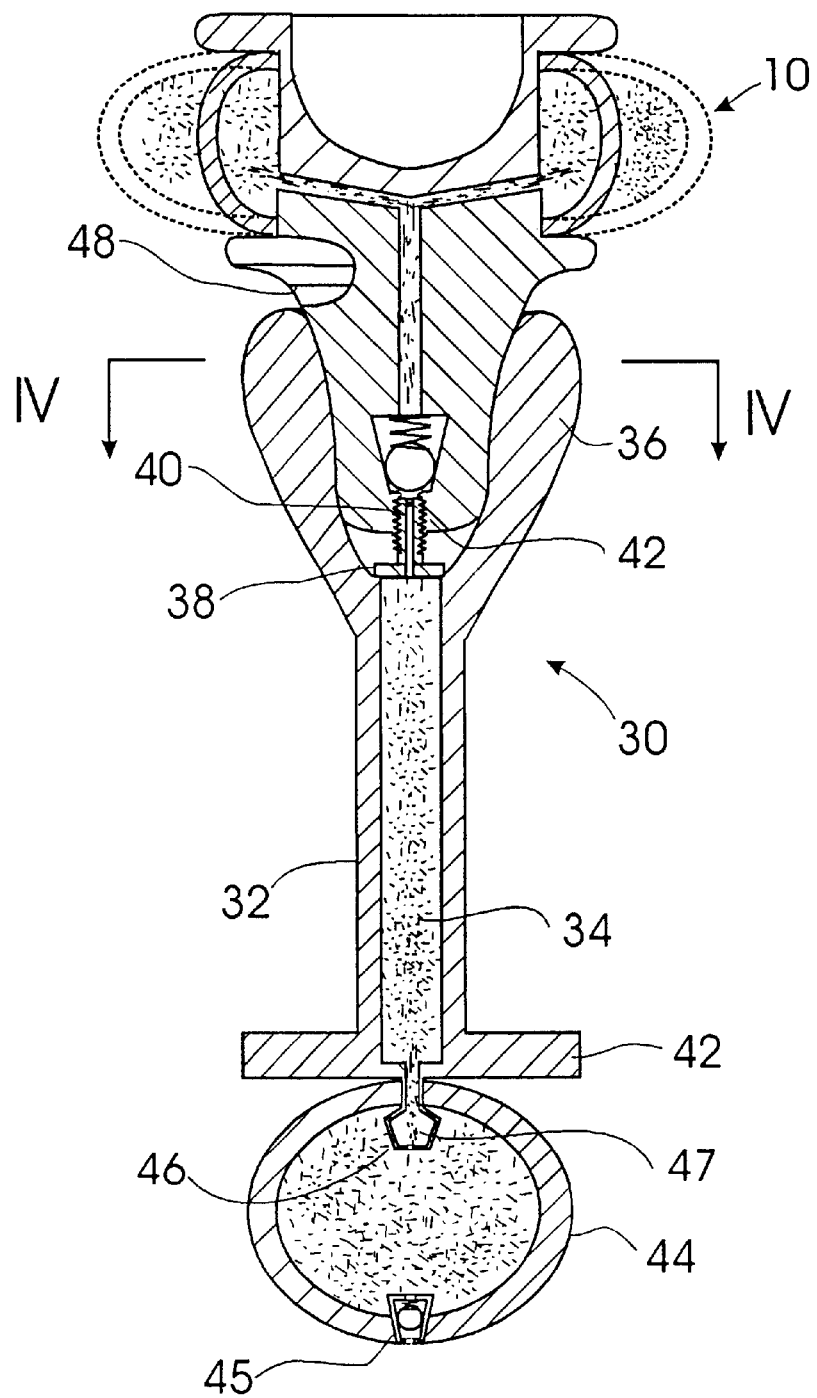
FIG. 4 is a longitudinal sectional view of the inflatable pessary of FIG. 1 connected to a mechanical insertion device prior to insertion into the patient's vagina.

The device of the embodiment shown in FIGS. 1, 3 and 4 operates as follows. Prior to insertion of the pessary into the patient's vagina, the pessary 10, with an inflatable portion 12 in its deflated form shown by solid lines in FIG. 1, is attached to the pessary insertion/removal device 30 by screwing the threaded stem 40 of the device 30 into a threaded opening 19 of the pessary. This operation is performed by inserting the tapering end 14 of the pessary 10 into the tapered opening of the funnel-like finder 36 so that the threaded stem 40 of the device 30 is aligned with the threaded opening 19, and then the stem 40 is screwed into opening 19 by rotating the device 30 with the use of a flange. The rotation is continued until the front end of the finder 36 is aligned with the matching mark 48 on the tapered portion 14 of the pessary 10. When rotation of the device 30 is discontinued in the position of alignment of the mark 48 with the end of the finder 36, the user of the device can be sure that the connection between the pessary 10 and the device 30 is sufficiently strong and that the check valve formed by the spring-loaded ball 21 is closed.

The pessary 10 supported by the device 30 is then easily inserted into the patient's vagina and adjusted to an appropriate position. The pessary is then inflated by periodically squeezing and releasing the pumping bulb 44. When the bulb is squeezed, the air which is entrapped in the bulb 44 and in the central axial opening 34 of the housing 32 is displaced under pressure towards the vaginal pessary 10 and lifts the ball 21 against the force of the spring 23. The air is then pumped into the inflatable portion 12 of the pessary 10 via the threaded opening 19, axial channel 16, and transverse channels 18. As a result, the inflatable part 12 of the pessary is inflated, its diameter is increased, and it assumes the form shown in FIGS. 1 and 4 by dash-and-dot lines. Due to an increased diameter, the pessary is fixed in the vaginal V in the selected position, e.g., as shown in FIG. 7. In its inflated state with an increase diameter the pessary compresses the urethra through the vaginal wall and thus reduces the cross section of the urethral lumen to the point where no urine leaks out during movement. Within the vagina V, the tapered portion 14 of the pessary 10 is directed towards the vaginal entrance.

Since the pessary 10 is fixed within the vagina V, the insertion/removal device 30 can be separated. For this purpose, the threaded stem 40 is unscrewed from the threaded opening 19 of the pessary by rotating the device 30 with the use of the flange 42 as a handle. Since the stem 40 and the opening 19 have non-locking thread, the device 30 can be disconnected from the pessary 10 fixed in the vagina without a noticeable effort, so that disconnection of the device 30 will not violate position of the pessary in the vagina V.

At the end of the day before the bed time, the patient easily reconnects the mechanism to the pessary 10 by inserting the device 30 into the vagina V so that the funnel-like finder 36 is fit onto the tapered portion 14 of the pessary and is then connected thereto by screwing the threaded stem 40 into the threaded opening 19 of the pessary 10. The flange 42 is rotated until the front edge of the device 30 overlaps the position of the mark 48 so that the end of the stem 40 pushes the ball 25 against the force of the spring 25, whereby the air is released from the inflated portion 12 of the pessary 10 via the channels 18, 20, channel 16 and a gap between the now lifted ball 21 and the open end of the threaded opening 19. After deflation, the diameter of the inflatable portion 12 is reduced to the condition shown by the solid lines in FIGS. 1 and 4, so that the pessary 10, which is now connected to the device 30, can be easily withdrawn from the vagina V.

Figures 5, 6:
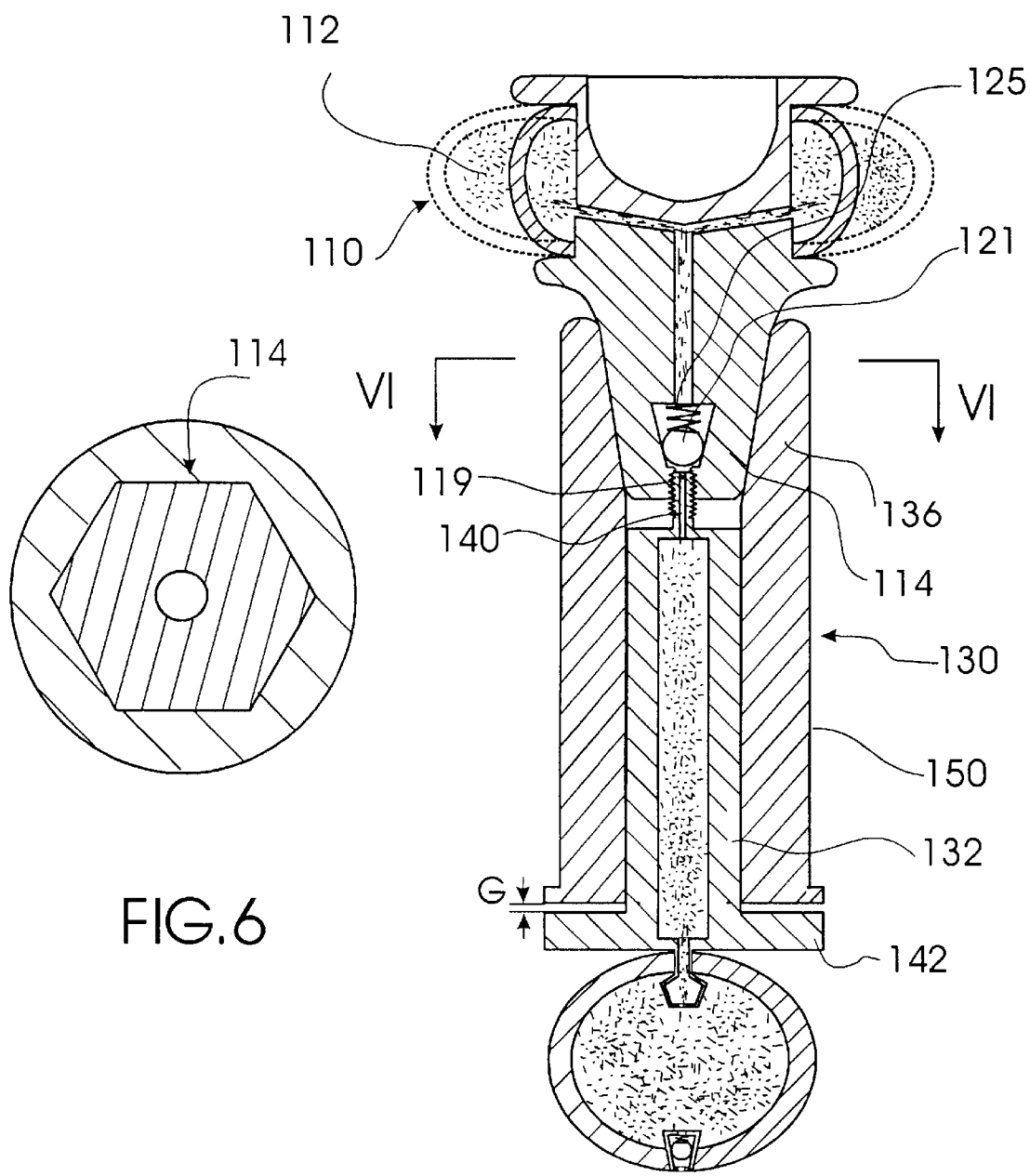
FIG. 5 is a longitudinal sectional view of a modified inflatable pessary connected to a pessary insertion/removal device made in accordance with another embodiment of the invention.
FIG. 6 is a sectional view along line VI—VI of FIG. 4.

FIGS. 5 and 6 illustrate another embodiment of the vaginal pessary and the pessary insertion/removal device. FIG. 5 is a longitudinal sectional view of a modified inflatable pessary connected to a pessary insertion/removal device made in accordance with another embodiment of the invention. FIG. 6 is a sectional view along line VI—VI of FIG. 5.

Since in general the pessary and the pessary insertion/removal device of this embodiment are similar to those of the previous embodiment, the parts of the embodiment of FIGS. 5 and 6 identical to those shown in FIGS. 1–4 will be designated by the same reference numerals with an addition of 100. Furthermore, the description of identical parts and elements will be omitted.

A pessary 110 of the embodiment of FIGS. 5 and 6 differs from the one shown in FIGS. 1–4 only by the non-round cross section of the tapered portion 114 of the pessary 110. As can be seen from FIG. 6, in the illustrated embodiment the tapered portion 114 has a hexagonal shape. The device 130 is in general similar to the device 30 of the previous embodiment and differs from it in that the finder portion 136 is separated from the hollow tubular housing 132 and is formed on the end of an outer housing 150 which faces the tapered portion 114 of the pessary 110. The opening of the funnel-like finder 136 has the same non-round cross section as the tapered end 114 of the pessary 110, which is hexagonal in this embodiment. The hollow threaded stem 140 is formed on the closed front end of the tubular housing 132 which is telescopically inserted into the outer housing 150. The rest of the device remains the same as in the previous embodiment.

In use, prior to insertion, the device 130 is connected to the pessary 110 by inserting the tapered portion 114 into the finder 136. Since the tapered end 114 of the pessary 110 and the opening of the finder 136 have mating hexagonal profiles, the finder 136 will fit onto the tapered end as an Allen wrench is fit onto the hexagonal head of the bolt, so that the relative rotation between the pessary 110 and the outer housing 150 is prevented. By holding with one hand the pessary 110 and the outer housing 130 in the region of the finder 136, the stem 140 is screwed into the threaded opening 119 of the pessary by rotating the flange.

The flange is rotated until a small gap G, e.g., of about 2 to 5 mm remains between the front edge of the flange 142 and the rear end face of the outer housing 150. A provision of this gap guarantees that the end of the stem did not lift the ball 121 against the force of the spring 125.

The pessary 110, which is a deflated state, is inserted into the patient's vagina, is inflated in the same manner as in the previous embodiment, and is then easily disconnected by rotating the flange 142 in the direction of unscrewing the stem 140 from the threaded opening 119.

For removal of the pessary 110 from the patient's vagina, the profiled finder 136 is fit onto the profiled tapered end 114 of pessary 110 so that the pessary cannot be rotated with respect to the outer housing 150. The outer housing 150 is held with one hand of the user and the flange 142 is then rotated by another hand of the user in the direction of screwing the threaded stem 140 into the threaded opening 119. The flange 142 is rotated until its front surface comes into contact with the rear end face of the outer housing 150 so that no gap G is left between both parts. Under these conditions, the front end of the hollow threaded stem 140 lifts the ball 121 against the force of the spring 125, whereby air is released from the inflated portion 112 of the pessary 110. In a deflated state, the pessary 110 is removed from the vagina by withdrawing the device 130 from the vagina together with the reconnected pessary 110.

Thus it has been shown that the invention provide an inflatable vaginal pessary which can be easily inserted into and removed from the patient's vagina without the use of fingers but with the use of a simple mechanical device by a patient herself, which is disconnected from the device after inflation and during the use of the pessary, which can be easily reconnected to the pessary removing device, can be adjusted to a required position within the patient's vagina, can be connected to a mechanical device for its insertion and removal. The invention also provides a method for easy and reliable insertion of the pessary by the patient herself.

Although the invention has been shown and described with reference to specific embodiments, it is understood that these embodiments should not be construed as limiting the application of the invention, so that any changes and modifications are possible, provided they do not depart from the scope of the patent claims. For example, the pessary may be made without the recess on the front side of the inflatable portion, the tapered guide portion of the pessary may have a square, triangular, hexagonal, splines, or any other cross-section. The housing of the pessary insertion/removal device may have any modified shape and made of biologically-acceptable plastic or metal. The device can be connected to the pessary by having a thread on the outer side of the tapered portion and on the inner surface of the finder, while the ball of the check valve is lifted by a non-threaded stem.

What is claimed is:

1. The device for installation and removal of an inflatable vaginal pessary into and from the patient's vagina, said inflatable vaginal pessary having an inflatable portion, a guide portion connected to said inflatable portion, and connection means for connecting to said device, said device comprising:

a hollow tubular housing having a funnel portion on one end for engagement with said guide portion of said inflatable vaginal pessary;

means for removably connecting said device to said connection means of said inflatable vaginal pessary on said one end; and a pumping means on the other end of said hollow tubular housing for pumping a fluid under pressure into said inflatable portion of said vaginal pessary.

2. The device of claim 1, wherein said means for removably connecting said device to said connection means comprises a threaded tubular extension.

3. The device of claim 1, wherein said other end of said hollow tubular housing has means for sealingly and removably connecting said pumping means to said other end of said hollow tubular housing.

4. The device of claim 3, wherein said fluid is air from the surrounding atmosphere and said pumping means comprises a resilient hollow bulb having a check valve for admission of air into said pumping means when said pumping means is released after squeezing.

5. The device for installation and removal of an inflatable vaginal pessary into and from the patient's vagina, said inflatable vaginal pessary having an inflatable portion, a guide portion of a non-round cross-section connected to said inflatable portion, and connection means for connecting to said device, said device comprising:

a hollow tubular outer housing having a funnel portion on one end for engagement with said guide portion of said inflatable vaginal pessary, said funnel portion having the same non-round cross section as said non-round cross-section of said guide portion of said pessary;

a hollow tubular inner housing telescopically inserted into said hollow tubular outer housing;

pumping means for pumping fluid under pressure into said inflatable portion of said pessary, said pumping means being located outside of said hollow tubular outer housing and is removably attached to one end of said hollow tubular inner housing; and means for removably connecting said device to said connection means of said inflatable vaginal pessary on the other end of said hollow tubular inner housing which is opposite to said one end.

6. The device of claim 5, wherein said means for removably connecting said device to said connection means comprises a threaded tubular extension.

7. The device of claim 6, wherein said other end of said hollow tubular inner housing has means for sealingly and removably connecting said pumping means to said other end of said hollow tubular inner housing.

8. The device of claim 5, wherein said fluid is air from the surrounding atmosphere and said pumping means comprises a resilient hollow bulb having a check valve for admission of air into said pumping means when said pumping means is released after squeezing.

9. A combination of an inflatable vaginal pessary with a device for inserting and removing said vaginal pessary into and from the patient's vagina, wherein:

said inflatable vaginal pessary comprises:

an inflatable portion having an inflatable chamber;

a guide portion connected to said inflatable portion and having a channel for the supply of fluid under pressure into said inflatable chamber, said channel having one end connected to said inflatable chamber and another end opened to the atmosphere;

a check valve at said another end of said channel for admission of said fluid under pressure into said inflatable chamber and for preventing said fluid under pressure from escaping from said inflatable chamber; and means for connecting a pessary installation and removal device to said pessary;

said device comprises:

a hollow tubular housing having a funnel portion on one end for engagement with said guide portion of said inflatable vaginal pessary;

means for removably connecting said device to said connection means of said inflatable vaginal pessary on said one end; and a pumping means on the other end of said hollow tubular housing for pumping a fluid under pressure into said inflatable portion of said vaginal pessary.

10. The combination of claim 9, wherein said inflatable portion in its inflated state has a diameter greater than a diameter of said guide portion, said guide portion having a tapered shape which is tapered in a direction away from said inflated portion.

11. The combination of claim 10, wherein said check valve comprises a ball and a spring, said another end of'said channel has an outlet to the atmosphere which has a diameter smaller than said ball, said spring constantly urging said ball toward said outlet for closing connection of said channel with the atmosphere.

12. The combination of claim 11, wherein in said vaginal pessary said means for connecting comprises a thread at said another end of said channel.

13. The combination of claim 11, wherein said thread is a no-locking thread.

14. The combination of claim 13, wherein said means for removably connecting said device to said connection means of said inflatable vaginal pessary comprises a threaded tubular extension.

15. The combination of claim 9, wherein said other end of said hollow tubular housing has means for sealingly and removably connecting said pumping means to said other end of said hollow tubular housing.

16. The combination of claim 15, wherein said fluid is air from the surrounding atmosphere and said pumping means comprises a resilient hollow bulb having a check valve for admission of air into said pumping means when said pumping means is released after squeezing.

17. A combination of an inflatable vaginal pessary with a device for inserting and removing said vaginal pessary into and from the patient's vagina, wherein:

said inflatable vaginal pessary comprises:
an inflatable portion having an inflatable chamber;
a guide portion of a non-round cross section connected to said inflatable portion and having a channel for the supply of fluid under pressure into said inflatable chamber, said channel having one end connected to said inflatable chamber and another end opened to the atmosphere;
a check valve at said another end of said channel for admission of said fluid under pressure into said inflatable chamber and for preventing said fluid under pressure from escaping from said inflatable chamber; and
means for connecting a pessary installation and removal device to said pessary;

said device comprises:
a hollow tubular outer housing having a funnel portion on one end for engagement with said guide portion of said inflatable vaginal pessary, said funnel portion having the same non-round cross section as said non-round cross-section of said guide portion of said pessary;
a hollow tubular inner housing telescopically inserted into said hollow tubular outer housing;
pumping means for pumping fluid under pressure into said inflatable portion of said pessary, said pumping means being located outside of said hollow tubular outer housing and is removably attached to one end of said hollow tubular inner housing; and
means for removably connecting said device to said connection means of said inflatable vaginal pessary on the other end of said hollow tubular inner housing which is opposite to said one end.

18. The combination of claim 17, wherein said means for removably connecting said device to said connection means comprises a threaded tubular extension.

19. The combination of claim 18, wherein said other end of said hollow tubular inner housing has means for sealingly and removably connecting said pumping means to said other end of said hollow tubular inner housing.

20. The combination of claim 19, wherein said fluid is air from the surrounding atmosphere and said pumping means comprises a resilient hollow bulb having a check valve for admission of air into said pumping means when said pumping means is released after squeezing.

\* \* \* \* \*